United States Patent
Zedda

[11] Patent Number: 5,310,340
[45] Date of Patent: May 10, 1994

[54] FIXED LINGUAL ORTHODONTIC APPLIANCE

[76] Inventor: Paolo F. Zedda, Sinnai (Cagliari), Italy

[21] Appl. No.: 37,892
[22] Filed: Mar. 26, 1993
[51] Int. Cl.$^5$ .............................................. A61C 3/00
[52] U.S. Cl. ........................................ 433/8; 433/9; 433/18; 433/24
[58] Field of Search ................ 433/8, 9, 18, 2, 24, 433/215

[56] References Cited

U.S. PATENT DOCUMENTS

| | | |
|---|---|---|
| 2,266,860 | 12/1941 | Griesinger . |
| 2,318,001 | 5/1943 | Linde . |
| 3,936,939 | 2/1976 | Faunce . |
| 4,197,644 | 4/1980 | Ackerman, Jr. . |
| 4,202,328 | 5/1980 | Sukkarie ................. 433/18 |
| 4,230,104 | 10/1980 | Richter .................. 433/18 |
| 4,337,037 | 6/1982 | Kurz . |
| 4,386,908 | 6/1983 | Kurz ..................... 433/8 |
| 4,470,809 | 9/1984 | Klepacki ................. 433/9 |
| 4,496,317 | 1/1985 | Hulsey . |
| 4,533,320 | 8/1985 | Piekarsky ................ 433/9 |
| 5,163,839 | 11/1992 | Metcalf .................. 433/9 |

*Primary Examiner*—John J. Wilson
*Attorney, Agent, or Firm*—Darby & Darby

[57] ABSTRACT

The invention relates to a fixed lingual orthodontic appliance which, when installed on the patient, rests on the lingual surface of the teeth and the palatine and inferior alveolar mucous membranes, comprising a base and support element (1) destined to be rested on the oral mucous membrane, substantially horseshoe-conformed, a plurality of elastic connecting elements (2) made by the modelling of a steel wire or similar with predetermined elastic characteristics, fixed at an end to the base and support element (1), and at the other of its ends on a respective bracket (3), the bracket or brackets (3) being made in synthetic resin and in a number which is equal to that of the teeth to be treated, and being conformed in such a way as to exhibit a concave face (7) which will be cemented on the equally concave lingual surface of the tooth, the other, convex, face (8) exposed to the oral cavity being superficially perfectly smooth and having a convexity which is equal to the development of the corresponding surface of the tooth.

9 Claims, 2 Drawing Sheets

FIXED LINGUAL ORTHODONTIC APPLIANCE

The invention relates to a new fixed orthodontic appliance able to guide with considerable precision even complex dental movements by means of a guide structure which is completely invisible from the outside.

The prior art embraces intraoral orthodontic appliances able to produce orthodontic movements, that is, the movement of one or more teeth (generally for therapeutic-corrective reasons) through the application of a calibrated force aimed at guiding the dental movement itself.

The appliances which are today in use are divisible into two categories: fixed and mobile appliances.

The former are installed and modified only by the orthodontist and are worn by the patient for the entire duration of the treatment.

These are essentially constituted by metallic brackets, which are cemented on the vestibular or lingual surface of the teeth to be treated, and by a special steel wire, selected on the basis of predetermined elastic characteristics and having round or rectangular section, which steel wire is passed through a special slot present on each bracket and thus fixed in such a way as to allow the wire to run through it.

The orthodontic wire can thus be modelled with special appliances and is equipped with an elevated elastic memory, for which reason, once it is fixed on the teeth, if it undergoes a distorsion which is below the elastic deformation limit, it tends to return to its equilibrium conformation, guiding in this way the orthodontic movement. Elastics and springs can also be applied to the brackets, as well as other conventional means, which impress mutual attraction or repulsion between bracket and bracket, bracket and orthodontic arch, bracket or orthodontic arch and intraoral or extraoral activators. In this way, through a correct use of the fixed orthodontic appliance, it is possible to control the movements of each single dental element (or tooth), in the three spatial planes, and to treat the most serious orthodontic problems, or in any case those instances where contemporaneous control over several dental movements is required. During the last ten years a fixed lingual orthodontic technique has been developed, which substantially differs from the above-described vestibular technique because of the fact that it is installed on the lingual surface of the teeth and is thus invisible externally. Thus it possesses, with respect to the preceding technique, undoubted aesthetic advantages, but it is little used since it cannot guarantee the degree of precision necessary, it requires long periods to model and especially, because it obstructs phonation. For this reason the appliance, though not easily visible, is immediately intelligible as soon as the patient begins to speak. Furthermore, the lingual brackets are irritating to the lingual mucous membrane and constitute retentive structures for oral bacterial plaque.

The mobile orthodontic appliances, or removable appliances, are instead largely constituted by plates, generally made in resin, which are fixed to the teeth, not stably, by means of flexible metallic hooks and they can be worn by the patient only for a few hours per day. However the control of the orthodontic movements induced in this way is imprecise.

The aim of the present invention is thus that of eliminating the above-mentioned drawbacks by providing a new fixed orthodontic appliance of the lingual type, aimed at:

obtaining an effective therapeutic-corrective treatment but at the same time being invisible and unintelligible during the course of normal interpersonal relations;

not being irritating to the oral mucous membranes with which it comes into contact;

allowing normal phonation.

The invention, as it is characterised in the claims which follow, solves the problem of providing a fixed lingual orthodontic appliance, from a general point of view, and is characterised in that it comprises:

a base and support element 1 destined to rest on the oral mucous membrane, substantially horseshoe-conformed, having a thickness which is inferior to its transversal breadth, and following conformingly and at the distance of a few millimeters the progression of the dental arch, upper and lower, in its morphological development;

a plurality of elastic connecting elements 2, realised through modelling of a steel wire or similar with predetermined elastic characteristics, at one end rigidly fixed in channels or holes 4 correspondingly presented by the said base and support element 1 and at the other end fixed on a respective bracket 3, arranged in such a way as to be near or more or less adherent to the gingival mucous membrane 6 along all of its morphological development;

a plurality of brackets 3 realised in synthetic resin and in number equal to that of the teeth to be treated, conformed so as to exhibit a concave face 7, destined to be cemented on the same lingual surface of the tooth, the other, convex face 8, exposed to the oral cavity, being superficially perfectly smooth and with a convexity which conforms to the development of the corresponding surface of the tooth;

said elastic connecting elements 2 being envisaged in a number at least equal to the number of the brackets 3 and the relative teeth to be treated and said channels or holes 4 being envisaged on the said base and support element 1 in a number corresponding to the number of elastic connecting elements 2 to be fixed and corresponding in position to the relative brackets 3.

The invention is described in more detail in the following description with the help of the accompanying drawings, which represent a non-limiting example of a preferred embodiment, and in which.

Figure 1:
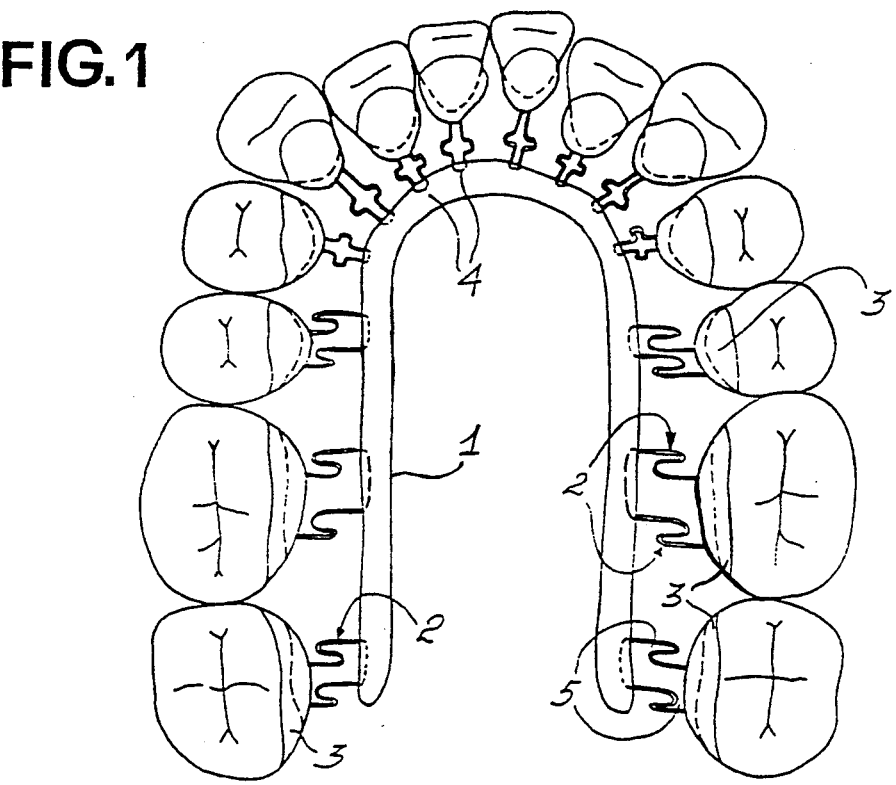
FIG. 1 shows a schematic view from above of the appliance object of the present invention applied on the lower dental arch.
Figure 2:
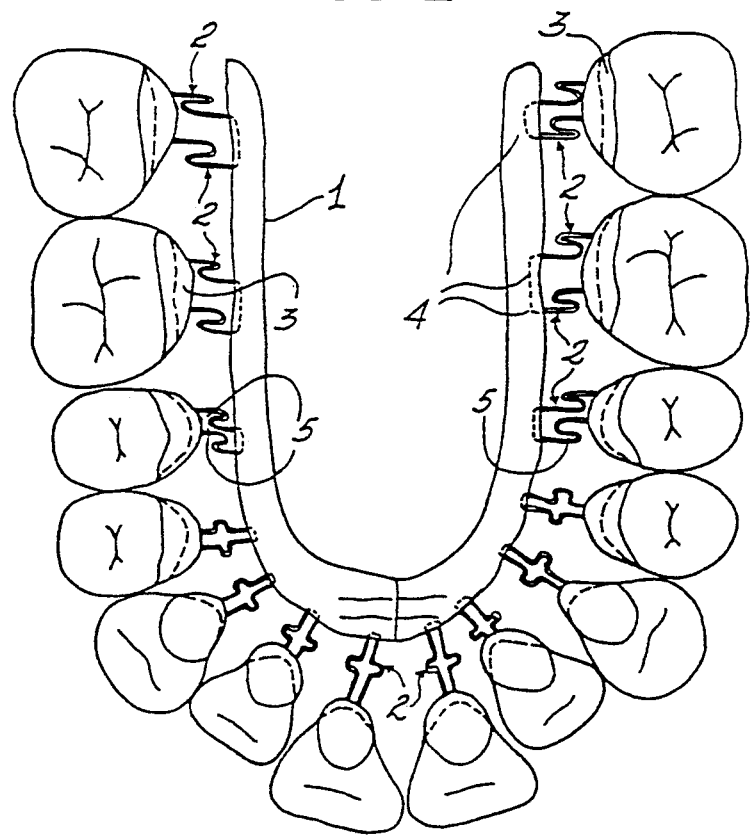
FIG. 2 shows, in a schematic view from below, the appliance of the present invention applied on the upper dental arch.

With reference to the drawings, the orthodontic appliance of the present invention as illustrated in FIGS. 1 and 2 comprises a base and support element 1, several elastic connecting elements 2, these latter being connected to at least an equal number of brackets 3 applied to the teeth, and thus comprising several brackets 3, in a number equal to the teeth to be treated. The base and support element 1 is preferably made in a metallic alloy or resin suitable for orthodontic appliances, is of a flattened-horseshoe shape, is of a thickness which is less than that of its transversal breadth, and is destined to be leant on the oral mucous membrane following more or less, at a distance of a few millimeters, the progression of the dental arch in its development. The base and support element 1 is preferably obtained with the same technique and same type of alloys or resins used today to construct skeletal dentures, in such a way as to be, once installed, perfectly adherent to the palatine or mandibular mucous membrane. The modest breadth of the base and support element (approximately 0.5–3.5 mm) and the progression of the free surface which simulates the oral mucous membrane render the said support 1 very tolerable and not obstructive to the movements of the tongue.

The elastic connecting elements 2 are made using a special steel wire or similar, with predetermined elastic characteristics, of the type presently in use for orthodontic appliances; excellent results have been obtained with a nickel-titanium alloy wire.

The elastic connecting elements 2 are rigidly fixed or cemented at one end with resin or cement, in the said base and support element 1, while at their other ends they are fixed on a respective bracket 3, or better, as will be described hereinafter, the end of the elastic connecting element 2 is introduced and immovably fixed in the body of the relative bracket 3.

The elastic connecting elements 2 are made with round or rectangular section wire, of the same type, as has already been mentioned, as that used for the preparation of the prior art vestibular fixed appliances, and they can be present in numbers of one, two or more for each tooth and according to the mechanical characteristics required.

The elastic connecting elements 2 can be made with several types of wire with differing elastic properties according to the range of movements which is desired and according to the oppositely-directed resistance of the root surface of the tooth to be moved. Such variations may regard several elastic connecting elements 2 associated to several teeth, or even several elements 2 associated to the same tooth. The dentist will choose each time the most suitable wire for each elastic connecting element 2, for each tooth and for each phase of treatment.

Figure 3:
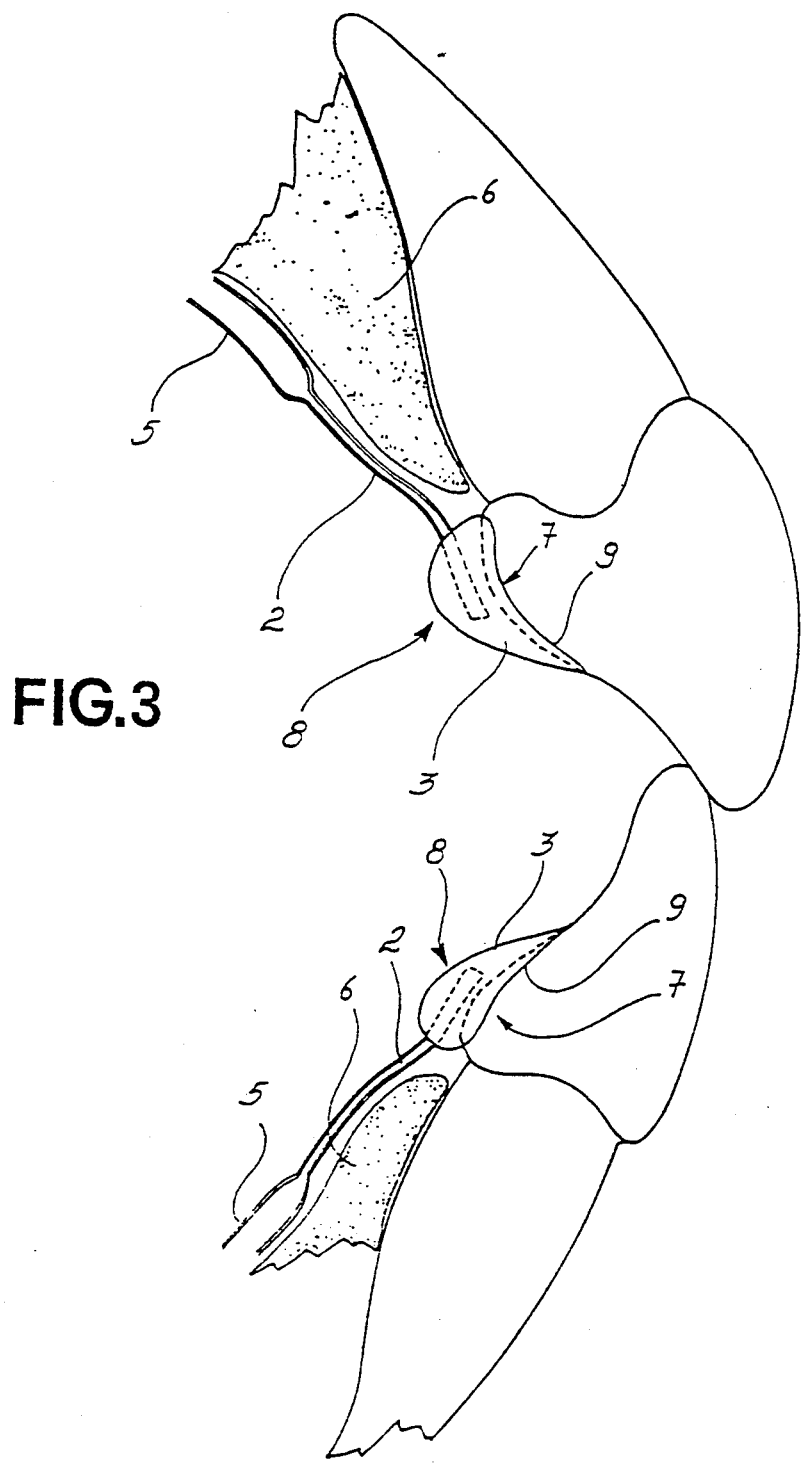
FIG. 3 shows a particular of the appliance on an upper incisor and also shows the relative lower incisor.

Each elastic connecting element 2 exhibits at least a small kink 5 which has a retaining function and which makes the bracket 3 connecting element 2 fixing stable. Each elastic connecting element 2, furthermore, is modelled in such a way as to assume, in normal projection to the gingival mucous membrane, denoted by 6 in FIG. 3, an almost straight development, or to exhibit one or more kinks 5 according to the need for stability and the elastic action to be exerted on the tooth. It must however stay close to or adhere to the mucous membrane along its entire development. The brackets 3, as illustrated in the accompanying figures, are made in resin, The brackets 3 exhibit two faces (FIG. 3): one face is concave 7 to be cemented on the enamel of the tooth, the other convex 8 and exposed to the oral cavity. The face 7 to be cemented reproduces morphologically exactly the dental surface on which it is destined to be fixed. The convex face 8 is, on the contrary, perfectly smooth so that it simulates perfectly the curvature of the tooth, thus avoiding irritation of the mucous membranes, phonation difficulties, retention of bacterial plaque and/or food residue. The two faces 7 and 8 converge gently to form a sharp, almost cutting edge 9 so that the bracket 3, once cemented on the tooth, does not offer a step which can be felt in the tooth-bracket joining area.

In practice, for the preparation and construction of the appliance according to the invention, the procedure is as follows: the elastic connecting elements 2 are modelled in such a way as to be adherent or almost so on the part of the patient's therapeutic set-up model which reproduces the oral mucous membrane, and are positioned detached by about 0.2 mm from the surface of the plaster which reproduces the lingual surface of the interested tooth. Thus the brackets 3 are welded or fixed with resin or cement in the position in the corresponding channels or holes 4 of the base and support element 1. At this point the liquid resin is made to drip on the lingual surface of each dental model in such a way as to fill the interstice between the wire of the elastic connection element 2 and the lingual surface of the tooth up until the terminal part of the said lingual surface is submerged. Then, once the resin has hardened, the finishing of the bracket 3 is proceeded with, its being shaped with rotating instruments mounted on a dentist's drill in order to obtain the above-described structural characteristics. Thus "made to measure" brackets are obtained.

Functionally, the base and support element 1 performs two tasks:
  it is the structure which keeps the elastic connecting elements 2 together and on which the reaction forces exerted by the same elements 2 15 unload;
  it functions as an extradental anchoring structure which is indispensable for obtaining the distalising of the molars.

Each elastic connecting element 2 must be modelled with regard to the number and type of kinks 5 which must be made, so that:
  each element 2 is kept as adherent as possible for the entire course of the treatment to the oral mucous membrane 6. The interstice between the wire and the mucous membrane must not be much above the movement in lingual-vestibular direction which the wire will undergo in accompanying the dental movement in order to permit of a slight deformation of the wire during the treatment, but it must not be irritating to the mucous membrane or obstruct phonation;
  it results passive on the arch at the end of the treatment, that is it is in a condition of elastic equilibrium if installed on a dental arch model which is equal to the dental arch itself in the conformation which it is desired to reach at the end of the treatment, or at the end of that particular phase of the treatment.

The orthodontic appliance object of the present invention is activated and applied in the following way:
  a plaster model is made of the two dental arches of the patient to be treated;
  using prior art techniques the dental model of the teeth to be treated is made, wherein the teeth are fixed in the position which will be the final position at the end of the treatment—thus the "therapeutic set-up model" is obtained;
  the elastic connecting elements 2 are modelled on the said therapeutic model in such a way as to lean on or breast the model of the gingival mucous membrane and be removed from the lingual surface of the dental model by about 0.1–0.3 mm;
  the base and support element 1 and the said elastic connecting elements 2, provisionally assembled and mounted on the therapeutic model, are subjected to thermal treatment in a kiln, according to prior art means, with the aim of bettering the stability and the elastic memory of the modelled wire; during this procedure the wire can be kept still by keeping it immersed in a heat-resistant covering material of the type used in muffle kiln firing;

the elastic connecting elements 2 are fixed definitively to the base and support element 1 by welding or resin in the desired position; fixing by resin becomes necessary when the elastic connecting elements 2 are constructed with a non-weldable type of wire or if the base 1 is made of resin;

the brackets 3 are prepared in self-polymerising resin which is placed in melted form on the lingual surface of each dental model, in such a way as to cover the ends of the respective elastic connecting element or elements (FIG. 3), and finished after solidification as described above;

the completed appliance, according to the invention, is installed in the oral cavity of the patient by fixing the brackets 3 on the lingual surfaces of the respective teeth; in order to obtain a good fixing it is advisable first to etch and bond the lingual surface of all the teeth to be treated and in a successive phase, fix the brackets 3 with self-polymerising or photo-polymerising resin one at a time, keeping the bracket 3 still on the respective tooth for the entire duration of the hardening phase of the resin.

If necessary, according to existing methods, auxiliary elastics can be fixed on the patient on to lingual or vestibular buttons which integrate and/or facilitate the action of the new appliance. In this way, with the present appliance orthodontic movement is stimulated on each tooth so that at the end of the treatment phase the predetermined new positions are attained.

The activation, and thus the preparation of the therapeutic model, can be repeated during the course of each single orthodontic treatment.

In order to allow correct functioning of the appliance, it is necessary to evaluate carefully, not only the forces exerted on the teeth, but also the force and the moment resulting from the reaction forces exerted by the elastic connection elements 2 on the base and support element 1, which, if it has been activated well, must not be subjected to asymmetrical movements, nor must it tend to detach itself from the mucous membrane.

The appliance of the present invention offers numerous advantages with respect to any other orthodontic appliance presently in use, which advantages are:

it is completely invisible and unintelligible if not by a careful oral examination. This means that it can be used in the treatment of patients who are not willing to encounter the aesthetic problems which are characteristic of the fixed vestibular appliances presently in use, nor the phonation difficulties which are typical of the fixed lingual appliances and mobile plaques;

the appliance, when installed, has no sharp edges, nor rough surfaces, which on the contrary are present in all of the orthodontic appliances of the prior art. It is thus highly tolerable for the mucous membranes and permits easy and efficient oral hygiene, including the use of vertically-inserted dental floss;

the preparation technique of the "made to measure" brackets 3 and the activation of the appliance on the therapeutic model permit of very high precision in the induced dental movements;

all of the reaction forces completely unload on one single, almost rigid structure (the base and support element 1). It is thus simple to make the distribution of the result of the reaction forces exerted on the dental elements homogeneous. The anchorage offered by the base and support element 1 which rests on the mucous membranes renders the whole structure more stable. This is impossible in the prior art fixed appliances whose conjoining structure, that is the wire, is not rigid and transmits various reaction forces on to the different teeth;

it completely eliminates the problem of friction between wire and brackets 3.

Further, the appliance of the present invention has further functional characteristics and applicational advantages. The described structure with rigid common support structure and elastic connecting elements 2 independent for each tooth cannot be found in any of the prior art appliances, whether fixed or mobile. The base and support element 1 is made in thin rigid metal which simulates the palate, while in the prior art appliances it is made from the same wire which passes at about the height of the centre of the dental crowns and is raised by a few millimetres on the surface of the enamel, which is the cause of irritation of the mucous membranes and phonation disturbances. In the present invention, on the contrary, the base and support element 1 is arranged away from the teeth and is adherent to the mucous membrane so as to avoid this drawback. Further, the rigidity of the base and support element 1 permits the use of elastic connecting elements 2 which are independent from each other and different for each tooth.

Finally, according to the invention the elastic connecting elements 2 have a work position which is essentially vertical (FIG. 3), thus the wire does not pass transversally on the lingual surface on the teeth, but moves away from this neuralgic zone immediately with the aim of not obstructing its physiological functionality, and thus permits of moving the dental element along the direction of the arch without sliding on the bracket 3, thus eliminating the problem of friction, and finally it permits of the use of wires having elastic characteristics which are different for each different tooth, or different wires to model different elastic connecting elements 2 for the same tooth.

I claim:

1. A fixed lingual orthodontic appliance, characterized by the fact that it comprises:

a base and support element (1) destined to be rested on the oral mucous membrane, substantially horseshoe-conformed, having a thickness which is inferior to its transversal breadth, and which follows conformingly and at the distance of a few millimeters, the progression of the dental arch, upper and lower, in its morphological development;

a plurality of elastic connection elements (2), realized through modeling of a wire with predetermined elastic characteristics, at one end rigidly fixed to the said support element (1) and at another end fixed on a respective bracket (3), arranged in such a way as to be near or more or less adjacent to a gingival mucous membrane (6) along all of its morphological development;

a plurality of brackets (3) realized in synthetic resin and in number equal to that of the teeth to be treated, conformed exhibiting a concave face (7), destined to be cemented on the same lingual surface of the tooth, a convex face (8) exposed to the oral cavity, being superficially perfectly smooth and with a convexity which conforms to the development of the corresponding surface of the tooth; said elastic connecting elements (2) being envisaged in a number at least equal to the number of the brackets (3) and the relative teeth to be treated and a plurality of channels or holes (4) being envisaged on the said base and support element (1) in a number corresponding to the number of elastic connecting elements (2) to be fixed and corresponding in position to the relative brackets (3).

2. An appliance as in claim 1, characterised by the fact that the said elastic connecting elements (2) can be present in numbers of one or more for each tooth and for each relative bracket (3).

3. An appliance as in claim 2, characterised by the fact that the said elastic connecting elements (2) can be made from different types of wire with differing elastic properties, obtaining various elastic connecting elements (2) associated to respective different teeth or different elastic connecting elements (2) associated to the same tooth.

4. An appliance as in claim 1, characterised by the fact that the said elastic connecting elements (2) can be made from different types of wire with differing elastic properties, obtaining various elastic connecting elements (2) associated to respective different teeth or different elastic connecting elements (2) associated to the same tooth.

5. An appliance as in claim 1, characterised by the fact that the said elastic connecting elements (2) are modelled in such as way as to present at least one small kink (5) between the respective ends, one rigidly fixed to the said base and support element (1) and the other rigidly fixed to the respective said bracket (3).

6. An appliance as in claim 1, characterised by the fact that the said base and support element (1) is made in a metallic alloy which is suitable for orthodontic appliances, exhibiting a breadth which is comprised between 0.5 and 3.5 millimeters, its surface which is destined to adhere to the oral mucous membrane exhibiting a development which morphologically conforms to the said oral mucous membrane.

7. An appliance as in claim 1, characterised by the fact that two faces (7) and (8) of the said brackets (3) converge gently and describe a sharp, almost cutting edge (9), not therefore offering tangible steps in the tooth-bracket passage area.

8. An appliance as in claim 1, characterised by the fact that the said elastic connecting elements (2) are rigidly fixed to the respective bracket (3) by the burying of their corresponding end in the bracket (3) body itself.

9. An appliance as in claim 1, characterized by the fact that the said base and support element (1) is made in a resin which is suitable for orthodontic appliances, exhibiting a breadth which is comprised between 0.5 and 3.5 millimeters, its surface which is destined to adhere to the oral mucous membrane exhibiting a development which morphologically conforms to the said oral mucous membrane.

* * * * *